(12) United States Patent
Vollmer et al.

(10) Patent No.: US 10,420,532 B2
(45) Date of Patent: Sep. 24, 2019

(54) METHOD AND APPARATUS FOR CALCULATING THE CONTACT POSITION OF AN ULTRASOUND PROBE ON A HEAD

(71) Applicant: Brainlab AG, Munich (DE)

(72) Inventors: Fritz Vollmer, Munich (DE); Ingmar Thiemann, Los Altos, CA (US)

(73) Assignee: Brainlab AG, Munich (DE)

( * ) Notice: Subject to any disclaimer, the term of this patent is extended or adjusted under 35 U.S.C. 154(b) by 969 days.

(21) Appl. No.: 14/760,575

(22) PCT Filed: Jan. 23, 2013

(86) PCT No.: PCT/EP2013/051164
§ 371 (c)(1),
(2) Date: Jul. 13, 2015

(87) PCT Pub. No.: WO2014/114327
PCT Pub. Date: Jul. 31, 2014

(65) Prior Publication Data
US 2015/0351718 A1  Dec. 10, 2015

(51) Int. Cl.
*A61B 8/00* (2006.01)
*A61B 8/08* (2006.01)
*G06T 7/73* (2017.01)

(52) U.S. Cl.
CPC ............ *A61B 8/429* (2013.01); *A61B 8/0808* (2013.01); *A61B 8/0891* (2013.01);
(Continued)

(58) Field of Classification Search
CPC .................................. A61B 8/429; G06T 7/75
See application file for complete search history.

(56) References Cited

U.S. PATENT DOCUMENTS 5,409,005 A  4/1995  Bissonnette et al.
6,547,737 B2  4/2003  Njemanze
(Continued)

OTHER PUBLICATIONS

Adamson et al (Automatic intracranial space segmentation for computed tomography brain images).*
(Continued)

*Primary Examiner* — Joel F Brutus
(74) *Attorney, Agent, or Firm* — Tucker Ellis LLP

(57) ABSTRACT

A data processing method for calculating the contact position of a medical ultrasound transceiver on the head of a patient, comprising the steps of: a) acquiring ROI data which represent a region of interest (ROI) corresponding to at least a part of a vessel in a vascular structure; b) acquiring contact region data which represent a contact region for the ultrasound transceiver on the head, wherein the contact region corresponds to one or more acoustic windows; c) determining at least one target point in the region of interest; d) determining at least two entry points on the contact region; e) calculating a set of lines which comprises the lines between the two points of each respective possible pair consisting of one entry point and one target point; f) eliminating lines which pass through a bony structure other than the bone immediately beneath the contact region; g) calculating a score for each of the remaining lines; and h) selecting the entry point of the line with the highest score as the contact position of the ultrasound transceiver.

16 Claims, 2 Drawing Sheets

Figure 1:
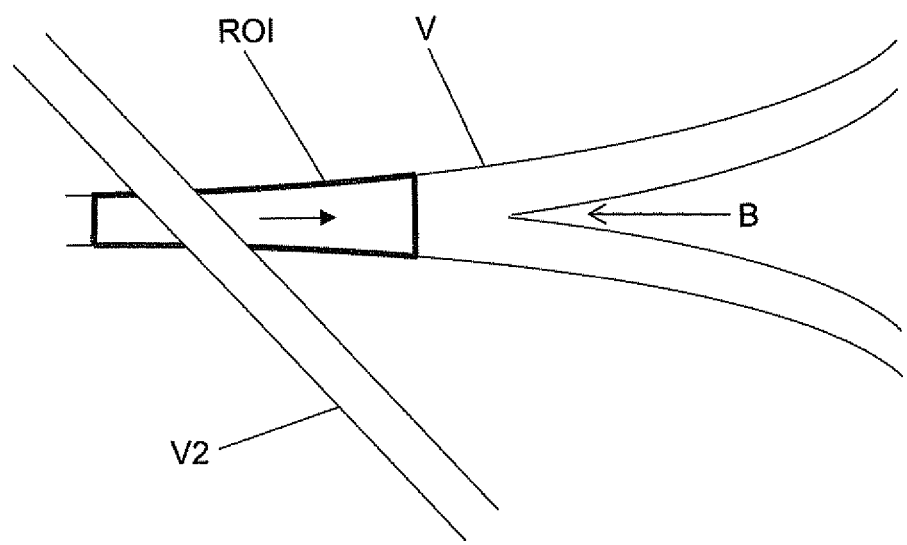

(52) U.S. Cl.
CPC .......... *A61B 8/4245* (2013.01); *A61B 8/4444* (2013.01); *A61B 8/469* (2013.01); *A61B 8/52* (2013.01); *G06T 7/75* (2017.01); *G06T 2207/10132* (2013.01); *G06T 2207/30016* (2013.01); *G06T 2207/30104* (2013.01)

(56) References Cited

U.S. PATENT DOCUMENTS

| | | | |
|---|---|---|---|
| 2008/0159604 A1* | 7/2008 | Wang | A61B 5/02007 382/128 |
| 2010/0160779 A1 | 6/2010 | Browning et al. | |
| 2011/0081057 A1* | 4/2011 | Zeng | G06T 7/0012 382/128 |

OTHER PUBLICATIONS

International Search Report and Written Opinion for International Application No. PCT/EP2013/051164 dated Oct. 17, 2013 (4 pages).
Neulen et al., "Image guidance to improve reliability and data integrity of transcranial Doppler sonography", Clinical Neurology and Neurosurgery, Aug. 2013, vol. 115, No. 8, pp. 1382-1388.
Vignon et al., "Mapping skull attenuation for optimal probe placement in transcranial ultrasound applications", Ultrasonics Symposium (IUS), 2009 IEEE International, Sep. 2009, pp. 2336-2339.

* cited by examiner

METHOD AND APPARATUS FOR CALCULATING THE CONTACT POSITION OF AN ULTRASOUND PROBE ON A HEAD

RELATED APPLICATION DATA

This application is a national phase application of International Application No. PCT/EP2013/051164 filed Jan. 23, 2013 and published in the English language.

The present invention relates to a data processing method for calculating the contact position of a medical ultrasound transceiver on the head of a patient, a computer program which implements said data processing method, and a computer.

Ultrasound imaging is an important medical imaging modality. It uses an ultrasound transceiver, also referred to as an ultrasound probe or ultrasound transducer, in contact with the skin of a patient. Unlike other modalities such as x-ray, ultrasound does not use ionising radiation. In addition, a Doppler shift of the reflected ultrasound beam can be used to examine the speed of the blood flow within a vessel. If a head is being examined, this is referred to as a transcranial Doppler (TCD) examination. However, ultrasound has the disadvantage that it can barely penetrate bones. The present invention therefore relates to finding a suitable position of the ultrasound transceiver on a patient's head in order to sound a region of interest in the head through the cranium.

In particular, the present invention relates to a data processing method for calculating the contact position of a medical ultrasound transceiver, also referred to as an ultrasound probe, on the head of a patient. The first step of the method involves acquiring ROI data which represent a region of interest (ROI) corresponding to at least a part of a vessel in a vascular structure. The region of interest can be defined by a single point, a plurality of points or a volume, wherein the volume can consist of adjacent and/or non-adjacent sub-volumes. The region of interest is preferably defined relative to the head, such that the ROI data represent the relative position between a point, a plurality of points or a volume and the head, in particular relative to the cranium. The vascular structure is known, for example from a suitable imaging modality, and is represented by a vascular structure dataset such as a three-dimensional image dataset.

The next step involves acquiring contact region data which represent a contact region for the ultrasound transceiver on the head, wherein the contact region corresponds to one or more acoustic windows. The contact region represents a region on the surface of the head on which the ultrasound transceiver can be placed. The contact region can be a continuous region or can be defined by non-adjacent sub-regions. The contact region is located over one or more acoustic windows. An acoustic window is a part of the cranium which exhibits a low thickness, such that it can more easily be penetrated by the ultrasound than other regions of the cranium.

The contact region can for example be determined from an atlas of the head or the cranium or from an image dataset of the head or the cranium which is generated using a suitable imaging modality. The atlas or the image dataset is preferably pre-registered with respect to the vascular structure dataset or is registered to the vascular structure dataset in a registration step which for example involves elastic image fusion. In another embodiment, the image dataset of the head or cranium and the vascular structure dataset are represented by a common dataset.

It is possible to automatically acquire the contact region data by identifying all possible acoustic windows. However, it is also possible to select only a subset of all the acoustic windows, wherein the subset for example comprises the acoustic windows which exhibit the smallest average thickness. It is also possible to manually select one or more acoustic windows.

The next step of the method involves determining at least one target point in the region of interest. If the region of interest is defined by one or more points, then this/these point(s) is/are used as the target point(s). If the region of interest is a volume, then at least one point within this volume is used as a target point. In one embodiment, a plurality of target points along the centre of the vessel are selected. In another embodiment, a plurality of target points on a cross-sectional area of the vessel are selected. Yet another embodiment can consist of a combination of the preceding two embodiments, i.e. can involve selecting a plurality of target points on a plurality of cross-sectional areas of the vessel. In yet another embodiment, a plurality of target points in the volume are selected according to either a random or a uniform distribution. In another embodiment, the target points can be set manually, for example in an image dataset of the region of interest which is displayed on a display.

The next step involves determining at least two entry points on the contact region. The entry points define possible contact positions of the ultrasound transceiver on the patient's head. In one embodiment, the entry points are inputted manually, for example in an image dataset which represents the contact region. In another embodiment, the entry points are determined automatically, for example by randomly or uniformly distributing a predetermined number of entry points over the contact region. In this embodiment, entry points can then optionally be shifted, added or deleted manually.

The next step involves calculating a set of lines which comprises the lines between the two points of each respective possible pair consisting of one entry point and one target point. In other words, the set of lines comprises all the lines which dedicatedly and directly connect one of the entry points and one of the target points. The lines therefore represent the path of the ultrasonic beam from all the entry points to all the target points. A line can therefore also be referred to as a trajectory in this document.

The next step involves eliminating lines which pass through a bony structure other than the bone immediately beneath the contact region. In other words, lines which pass through a bony structure other than the acoustic window are eliminated. Because the ultrasound is attenuated by bone, all lines or trajectories which pass through more than a required minimum amount of bone defined by the cranium, are deleted. This means that only lines passing through a minimum of bone remain.

The next step involves calculating a score for each of the remaining lines. This score is a value which represents how suitable the corresponding trajectory is for examining the target point using ultrasound. Examples of factors which affect the score are explained further below.

The next step involves selecting the entry point of the line with the highest score as the contact position of the ultrasound transceiver. This means that the best contact position for performing an ultrasound examination of the region of interest, in particular of the target point of the line with the highest score, is selected. It should be noted that it is also possible to equivalently use a negative score instead, in which case the line with the lowest score would be the most suitable for examining the region of interest, in particular the target point, and the entry point of the line with the lowest score would be selected as the contact position of the ultrasound transceiver.

Optionally, the entry point is provided to a medical navigation system in order to navigate the ultrasound transceiver to the calculated contact position. For this purpose, the ultrasound transceiver is provided with a marker device to be detected by the medical navigation system. Preferably, the target point corresponding to the line with the highest score is also provided to the medical navigation system. It is then possible not only to navigate the ultrasound transceiver such that it is located at the calculated contact position, but also to determine whether or not the ultrasound transceiver is orientated such that the ultrasonic beam is directed onto the target point.

The ultrasound transceiver is preferably calibrated, which means that the direction of the ultrasonic beam relative to the ultrasound transceiver is known to the medical navigation system. When the position of the patient is registered with the medical navigation system, the ultrasonic beam can be tracked in a (three-dimensional) patient dataset, such as an image dataset, by tracking the ultrasound transceiver. It should be noted that the ultrasonic beam can be a simple beam in the shape of a line or a beam covering a two-dimensional or three-dimension area, such as a fan beam.

In one embodiment, the ultrasound transceiver is tracked using a medical navigation system, such that the position of the ultrasound transceiver is known. The contact region represented by the contact region data is then selected on the basis of the position of the ultrasound transceiver. In one example, the contact region closest to the current position of the ultrasound transceiver is selected.

In another embodiment, the ultrasound transceiver is again tracked using a medical navigation system, such that the position of the ultrasound transceiver is known. It is then possible to determine whether or not the ultrasound transceiver is contacting the head at the determined contact position. There are several options if this is not the case. In accordance with a first option, the angle between the ultrasound transceiver and the head at which the ultrasonic beam reaches the region of interest is calculated. The ultrasound transceiver is preferably then navigated to this calculated angle.

In accordance with a second option, which can also be combined with the first option, a single entry point is derived from the current position of the ultrasound transceiver. The entry point is the point at which the ultrasonic beam emitted by the ultrasound transceiver at its current position enters the patient's head. The following steps are then performed: determining at least one target point in the region of interest; calculating a set of lines which comprises the lines between the two points of each respective possible pair consisting of the entry point and one target point; eliminating lines which pass through a bony structure other than the bone immediately beneath the contact region; and calculating a score for each of the remaining lines. In other words, scores are calculated for all the lines between the entry point corresponding to the current position of the ultrasound transceiver and the target points. The target point belonging to the line with the highest score is then the point to be aimed at by the ultrasound transceiver. If this score is lower than a predetermined threshold, a warning can be outputted in order to indicate that the region of interest cannot be examined from the current position of the ultrasound transceiver. If this second option is combined with the first option, then the target point belonging to the line with the highest score is used as the region of interest for calculating the angle.

In one embodiment, the method relates to measuring blood flow within a vessel and further comprises the step of eliminating from the set of lines those for which an intersection angle with a direction of the blood flow at the line's target point is outside a predetermined angular range. In order to cause a Doppler shift in the frequency of the ultrasonic beam reflected by blood cells flowing in the vessel, the ultrasonic beam must not be perpendicular to the blood flow direction. In order to achieve a reliable Doppler shift, a particular angular range between the blood flow direction and the ultrasound trajectory, for example between 20 and 60 degrees, is preferred. Any lines resulting in an intersection angle outside this predetermined angular range are therefore preferably eliminated. The angular range can be "half-open", such as for example a range limited by a maximum value only.

In one embodiment, the score of a line depends on the difference between the intersection angle of the line with a direction of the blood flow at the line's target point and a predetermined angle. This predetermined angle is preferably 30 degrees. The larger the difference between the intersection angle and the predetermined angle, the smaller the score of the corresponding trajectory.

In another embodiment, the score of a line depends on the length of a portion of the line which passes through a bony structure. In particular, the length of a portion or portions of the trajectory passing through a bony structure are integrated along the line. The longer the portion passing through a bony structure, the smaller the score of the corresponding line. In this document, the term "portion" encompasses both a single portion, i.e. a part between two points on the line, and a plurality of non-adjacent sub-portions, i.e. the entirety of such multiple parts of the line, wherein each part is defined by two points on the line and different parts do not overlap.

In another embodiment, the method relates to measuring blood flow within a vessel and further comprises the step of eliminating from the set of lines those for which the target point is closer to a bifurcation of the vessel than a minimum bifurcation distance. A bifurcation of a vessel in the vascular structure can cause turbulence in the blood flow. The present invention therefore relates to finding a suitable position of the ultrasound transceiver on a patient's head in order to sound a region of interest in the head through the cranium. It is therefore advantageous to eliminate lines with target points which are too close to the bifurcation. Instead of eliminating such lines from the set of lines, it is also possible to consider the distance between a potential target point and a bifurcation in the step of determining at least one target point in the region of interest, i.e. points in the region of interest which are closer to the bifurcation than a minimum bifurcation distance are not used as target points. The minimum bifurcation distance can for example be 0.5 cm, 1 cm or 2 cm.

In another embodiment, the score of a line depends on the distance between the line's target point and a bifurcation of the vessel. For the reasons explained above, turbulence in the blood flow occurs in the vicinity of the bifurcation, which can compromise the Doppler examination, such that the blood flow speed determined does not correspond to the actual blood flow speed along the vessel. The closer the line's target point to a bifurcation, the lower the line's score. However, this relationship optionally only obtains up to a maximum distance between a target point and a bifurcation, such that the influence of the distance between the target point and the bifurcation is the same for all target points for which this distance is higher than the maximum distance.

In another embodiment, the method relates to measuring blood flow within a vessel and further comprises the step of eliminating from the set of lines those for which the target point is closer to a vessel other than a vessel represented by the region of interest than a predetermined minimum vessel distance. Due to the principles of ultrasound technology, blood flow close to the examined target point negatively influences the Doppler examination in that it compromises the determination of blood flow speed. Accordingly, an additional step in this embodiment deletes all lines for which the target point is in the vicinity of a secondary vessel which is not the vessel to be examined.

In another embodiment, the score of a line depends on the distance between the line's target point and a vessel other than the vessel represented by the region of interest. The lower the distance between the line's target point and the other vessel, the lower the score of the corresponding line. This does not fully exclude a line for which the target point is close to another vessel, but does degrade the line's score.

As outlined above, a way of acquiring the contact region data is to use a (segmented) atlas in which one or more acoustic windows are indicated. The contact region data can however also be acquired using a representation of the cranium, such as an atlas, which is matched to the patient's head, or an image dataset of the patient. These sets of information are examples of a bone dataset which represents the three-dimensional bone structure of the head. In one embodiment, the step of acquiring contact region data then comprises the steps of acquiring the bone dataset and performing a morphological erosion of the bone dataset by a predetermined thickness, wherein "morphological erosion" means thinning the bone, in particular in a direction orthogonal to the outer surface of the cranium. As a result, the bone as a whole is thinned by the predetermined thickness.

The next step involves performing a morphological dilation of the eroded bone dataset by the predetermined thickness, wherein "morphological dilation" means that the eroded bone is extended again by the predetermined thickness. However, the morphological dilation only extends the bone structure which is still present in the eroded bone dataset. Parts of the bone in the original bone dataset which exhibit a lower thickness than the predetermined thickness will completely vanish in the eroded bone dataset and will therefore not be extended again in the morphological dilation. This means that any part of the bone which was originally thinner than the predetermined thickness will not be present at all in the dilated bone dataset. The morphological dilation is also preferably performed in a direction perpendicular to the outer surface of the cranium.

The next step involves subtracting the dilated bone dataset from the original bone dataset. Since any part of the bone which is thicker than the predetermined thickness will be identical in the dilated bone dataset and the original bone dataset, these parts will be eliminated by the subtracting step. Only parts which are present in the original bone dataset but not in the dilated bone dataset, i.e. the parts of the bone which were originally thinner than the predetermined thickness, will remain after the subtracting step. The subtracting step therefore results in a dataset which represents only the regions of the cranium which are thinner than the predetermined thickness and thus qualify as acoustic windows. The predetermined thickness can be set to any appropriate value, such as for example 3 mm. This value optionally depends on at least one of the type of ultrasound transceiver and the ultrasound frequency. These parameters result in different bone penetration properties.

In one embodiment, the step of acquiring contact region data involves acquiring contact region data which represent a plurality of contact regions. The method steps between that of determining at least two entry points on the contact region and that of selecting the entry point of the line with the highest score as the contact position of the ultrasound transceiver are then repeated for each of the contact regions, in order to calculate a contact position of the ultrasound transceiver for each of the contact regions. It is thus possible in this embodiment for the same region of interest to be reached by an ultrasonic beam from different entry points in different contact regions, in particular through different acoustic windows. Using this approach, it is for example on the one hand possible to obtain a plurality of blood flow speed measurements from different entry points in order to increase the overall quality of the measurement by combining these different measurements. On the other hand, it is also possible to use the ultrasonic beam as a treatment beam emitted from different entry points onto the region of interest at the same time, in order to increase the effect of the ultrasonic treatment beam. It is then preferable to determine exactly one target point in the region of interest, such that the energy of a plurality of ultrasonic treatment beams is focused on this single target point.

In one embodiment, the step of acquiring ROT data involves acquiring a plurality of ROI data for a plurality of regions of interest. A set of lines is then calculated for each region of interest by repeating the step of calculating a set of lines an appropriate number of times. This results in a plurality of sets of lines. One line is then selected from each set of lines, such that the selected lines have a common entry point and the combined scores of the selected lines is maximised. The scores of the lines are preferably combined by adding or averaging the scores. The step of selecting the entry point then involves selecting the common entry point as the contact position of the ultrasound transceiver.

In this embodiment, a contact position of the ultrasound transceiver is calculated such that all the regions of interest can be examined using an ultrasound transceiver located at the calculated contact position. Optionally, the combined score of the selected lines is set to zero if the score of at least one of the selected lines is below a minimum score threshold. In this case, an entry point from which at least one region of interest cannot be examined satisfactorily is excluded from being selected as the contact position.

In one embodiment, the step of acquiring ROI data involves acquiring a plurality of ROI data for a plurality of regions of interest. The step of determining at least one target point then involves determining at least one target point in each of the regions of interest. The step of calculating a set of lines then involves calculating the set of lines which comprises the lines between the two points of each respective possible pair consisting of one entry point and one target point from the target points in all the regions of interest. In other words, the set of lines comprises the lines from an entry point to each target point in all the regions of interest for each possible entry point.

After any step of eliminating lines and before the step of calculating a score for each of the remaining lines, an additional step involves calculating a set of entry points comprising only the entry points which have remaining lines leading to each of the regions of interest. This means that entry points from which at least one region of interest cannot be examined are eliminated.

After the step of calculating a score for each of the remaining lines, an additional step involves calculating a subset of lines for each entry point in the set of entry points, wherein the subset of lines comprises only one line from each of the regions of interest to the corresponding entry point, such that the combined score for the lines in the subset of lines is maximized. In other words, an optimized subset of lines from the entry point to all the regions of interest is calculated for each entry point. The combined score is calculated as explained in the previous embodiment and again includes the option of setting the combined score to zero if the score of at least one line in the subset of lines is below a minimum score threshold.

The step of selecting the entry point then involves selecting the entry point for which the subset of lines has the largest combined score as the contact position of the ultrasound transceiver. In other words, the entry point from which all the regions of interest can be examined most satisfactorily is selected as the contact position.

The latter two embodiments include the option of determining a plurality of contact positions if no single entry point has lines leading to each of the regions of interest. The number of necessary contact positions is preferably minimized. Alternatively, the user can define a suitable trade-off between the number of contact positions and the (maximized) scores of the lines between the entry points corresponding to the contact positions and the regions of interest.

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

One advantage of the invention is that different examiners can take a measurement at exactly the same position, regardless of their experience in finding the anatomical region to be examined. The examiner does not have to decide the contact position personally, but is provided with a suitable contact position. This is an even clearer advantage if the ultrasound transceiver is navigated to the contact position. Using the same contact position is particularly advantageous in a clinical workflow, in which such examinations are performed repeatedly for monitoring purposes.

Typically, some parameters of the ultrasound transceiver can be adjusted. One of these parameters is the examination depth which indicates the depth at which the Doppler shift is to be detected. The examination depth parameter can optionally be determined and set on the basis of the distance between the entry point and the target point belonging to the line with the highest score. This allows the examination depth parameter to be automatically initialized. The parameter may then be adjusted by the examiner. In another option, the ultrasound transceiver is tracked using a medical navigation system, such that the position of the ultrasound transceiver is known. The examination depth parameter is then determined and set on the basis of the determined position of the ultrasound transceiver. These two options can also be combined, such that the initial value of the parameter is determined from the planned trajectory, and this value of the parameter is then revised on the basis of the tracked ultrasound transceiver.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements and optionally a volatile memory (in particular, a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

It is the function of a marker to be detected by a marker detection device (for example, a camera or an ultrasound receiver or analytical devices such as CT or MRI), such that its spatial position (i.e. its spatial location and/or alignment in up to three translational and/or up to three rotational dimensions) can be ascertained. The detection device is in particular part of a navigation system. The markers can be active markers. An active marker can for example emit electromagnetic radiation and/or waves, wherein said radiation can be in the infrared, visible and/or ultraviolet spectral range. The marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can also, however, exhibit a cornered—for example, cubic—shape.

A marker device can for example be a reference star or a pointer or one marker or a number of (individual) markers which are preferably in a predetermined spatial relationship. A marker device comprises one, two, three or more markers, wherein two or more such markers are in a predetermined spatial relationship. This predetermined spatial relationship is in particular known to a navigation system and for example stored in a computer of the navigation system.

An atlas typically consists of a plurality of generic models of objects, wherein the generic models of the objects together form a complex structure. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

In the field of medicine, imaging methods are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (so-called medical imaging modalities and/or radiological imaging methods) such as for instance computed tomography (CT) and cone beam computed tomography (CBCT; in particular volumetric CBCT), x-ray tomography, magnetic resonance tomography (MRT or MRI), conventional x-ray, sonography and/or ultrasound examinations, and positron emission tomography. Analytical devices are in particular used to generate the image data in apparatus-based imaging methods. The imaging methods are in particular used for medical diagnostics, to analyse the anatomical body in order to generate images which are described by the image data. The imaging methods are in particular used to detect pathological changes in the human body.

The method in accordance with the invention is in particular a data processing method. The data processing method is preferably performed using technical means, in particular a computer. The data processing method is in particular executed by or on the computer. The computer in particular comprises a processor and a memory in order to process the data, in particular electronically and/or optically. The determining and calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. In particular, the term "cloud" is used in this respect as a metaphor for the internet (world wide web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer.

The expression "acquiring data" encompasses in particular (within the framework of a data processing method) the scenario in which the data are determined by the data processing method or program. Determining data in particular encompasses measuring physical quantities and transforming the measured values into data, in particular digital data, and/or computing the data by means of a computer and in particular within the framework of the method in accordance with the invention. The meaning of "acquiring data" also in particular encompasses the scenario in which the data are received or retrieved by the data processing method or program, for example from another program, a previous method step or a data storage medium, in particular for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.) or via the interface (for instance, from another computer or a network). The data can achieve a state of being "ready for use" by performing an additional step before the acquiring step. In accordance with this additional step, the data are generated in order to be acquired. The data are in particular detected or captured (for example, by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The expression "acquiring data" can therefore also involve commanding a device to obtain and/or provide the data to be acquired. In particular, the acquiring step does not involve an invasive step which would represent a substantial physical interference with the body requiring professional medical expertise to be carried out and entailing a substantial health risk even when carried out with the required professional care and expertise. In particular, the step of acquiring, in particular determining, data does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably called "XY information" and the like.

Elastic fusion transformations (for example, image fusion transformations) are in particular designed to enable a seamless transition from one data set (for example a first data set such as for example a first image) to another data set (for example a second data set such as for example a second image). The transformation is in particular designed such that one of the first and second data sets (images) is deformed, in particular in such a way that corresponding structures (in particular, corresponding image elements) are arranged at the same position as in the other of the first and second images. The deformed (transformed) image which is transformed from one of the first and second images is in particular as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are in particular vectors of a deformation field. These vectors are determined by the optimisation algorithm which results in an optimum degree of similarity. Thus, the optimum degree of similarity represents a condition, in particular a constraint, for the optimisation algorithm. The bases of the vectors lie in particular at voxel positions of one of the first and second images which is to be transformed, and the tips of the vectors lie at the corresponding voxel positions in the transformed image. A plurality of these vectors are preferably provided, for instance more than twenty or a hundred or a thousand or ten thousand, etc. Preferably, there are (other) constraints on the transformation (deformation), in particular in order to avoid pathological deformations (for instance, all the voxels being shifted to the same position by the transformation). These constraints include in particular the constraint that the transformation is regular, which in particular means that a Jacobian determinant calculated from a matrix of the deformation field (in particular, the vector field) is larger than zero, and the constraint that the transformed (deformed) image is not self-intersecting and in particular that the transformed (deformed) image does not comprise faults and/or ruptures, and the constraint that if a regular grid is transformed simultaneously with the image and in a corresponding manner, the grid is not allowed to interfold at any of its locations. The optimising problem is in particular solved iteratively, in particular by means of an optimisation algorithm which is in particular a first-order optimisation algorithm, in particular a gradient descent algorithm. Other examples of optimisation algorithms include optimisation algorithms which do not use derivations such as the downhill simplex algorithm or algorithms which use higher-order derivatives such as Newton-like algorithms. The optimisation algorithm preferably performs a local optimisation. If there are a plurality of local optima, global algorithms such as simulated annealing or generic algorithms can be used. In the case of linear optimisation problems, the simplex method can for instance be used.

In the steps of the optimisation algorithms, the voxels are in particular shifted by a magnitude in a direction such that the degree of similarity is increased. This magnitude is preferably less than a predefined limit, for instance less than $\frac{1}{10}$ or $\frac{1}{100}$ or $\frac{1}{1000}$ of the diameter of the image, and in particular about equal to or less than the distance between neighbouring voxels. Large deformations can be implemented, in particular due to a high number of (iteration) steps.

The determined elastic fusion transformation can in particular be used to determine a degree of similarity (or similarity measure, see above) between the first and second data sets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can in particular be determined on the basis of a determined correlation between the first and second data sets.

It is within the scope of the present invention to combine one or more features of one or more embodiments to form another embodiment, wherever technically feasible.

The present invention shall now be explained in more detail by referring to the accompanying figures, which show:

FIG. 1 a section of a vascular system; and

Figure 2:
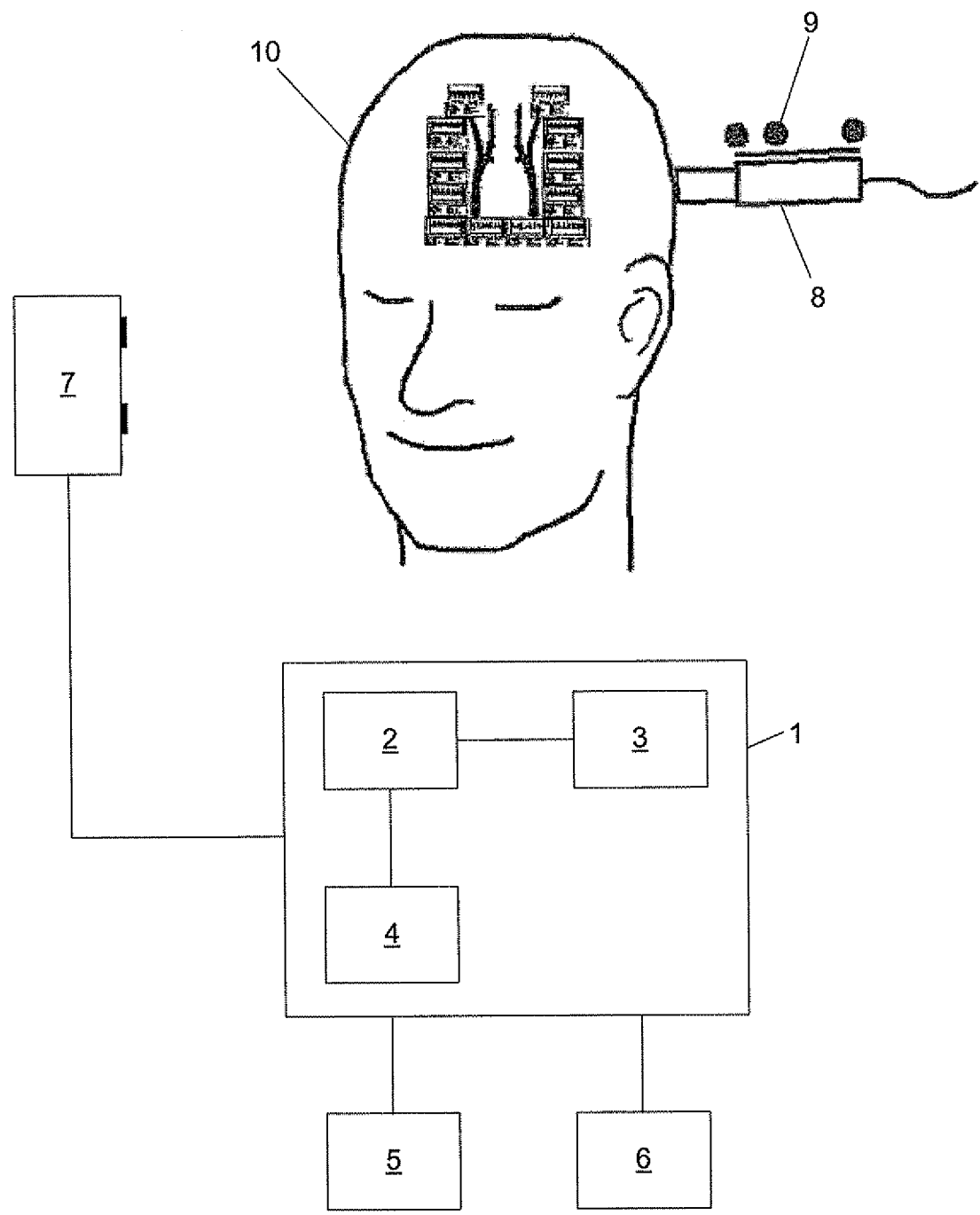

FIG. 2 an environment in which the invention is applied.

FIG. 1 shows a part of a vascular system within the head of a patient, specifically a part of a first vessel V and a part of a second vessel V2 which passes by the first vessel V. The first vessel V comprises a bifurcation B, such that the vessel V branches into two sub-vessels. The direction of the blood flow in the vessel V is indicated by an arrow. It is known that a transcranial Doppler (TCD) examination can be performed in order to determine the speed of the blood flow within the vessel V.

FIG. 2 schematically shows a scenario in which the present invention is implemented. The head 10 of a patient comprises a vascular system, a part of which is shown in FIG. 1. The TCD examination is performed using an ultrasound transceiver 8 which is provided with a marker device 9 which is registered with respect to the ultrasound transceiver 8. This means that the direction of the ultrasonic beam emitted from the ultrasound transceiver 8 can be determined from the position of the marker device 9.

The position of the marker device 9 is determined using a medical navigation system 7 which is known to the person skilled in the art and comprises means for detecting the marker device 9. In a typical configuration, the medical navigation system 7 comprises a light source which emits light which is then reflected by the marker device 9 and detected by a stereoscopic camera. The computer 1 can be part of the navigation system 7.

The present invention is embodied by a computer 1 comprising a central processing unit 2, a memory 3 and at least one interface 4. The computer 1 is connected via the interface 4 to an input device 5, such as a keyboard, a mouse or a touch screen, and/or to an output device 6 such as a monitor.

The memory 3 stores a program to be executed by the central processing unit 2 in order to perform the method steps of the present invention. Contact region data are also stored in the memory 3 which represent a contact region for the ultrasound transceiver 8 on the head 10, wherein the contact region corresponds to one or more acoustic windows. The contact region defines the region in which the ultrasound transceiver 8 can contact the head 10.

One way of obtaining the contact region data is to display an image of the head 10 on the output device 6 and manually identify the contact region using the input device 5. Another way is to use a generic atlas of the head in which the contact region is identified. The generic atlas is then matched to the actual patient's head 10 in order to adapt the atlas to the shape of the patient's head.

Yet another way of obtaining the contact region data is to acquire a bone dataset which represents the three-dimensional bone structure of the head 10. This bone dataset can be an image dataset, which can for example be acquired using a suitable imaging modality such as CT, or can be an atlas of the bone structure which is matched to the actual patient's head 10.

Morphological erosion by a predetermined thickness, such as for example 3 mm, is then performed on the original bone dataset. This erosion thins the bone structure by the predetermined thickness in a direction perpendicular to the outer surface of the bone structure. Preferably, the inner surface of the bone structure is eroded. Morphological dilation by the predetermined thickness is then performed on the eroded bone dataset. This thickens the remaining bone structure in the eroded bone dataset by the predetermined thickness. A portion of bone which was present in the original bone dataset but is no longer present in the eroded bone dataset is therefore not thickened by the morphological dilation. The morphological dilation is performed in the same direction as the morphological erosion and is likewise preferably applied to the inner surface of the bone structure. The effect of the morphological erosion and subsequent morphological dilation is that portions of bone which are thinner than the predetermined thickness are eliminated from the original bone dataset. Subtracting the dilated bone dataset from the original bone dataset thus results in a thin bone dataset which only comprises the parts of the original bone dataset which are thinner than the predetermined thickness. The thin bone dataset thus represents acoustic windows of the cranium which can be fully or partly used as the contact region. Optionally, the thickness of the skin around the cranium is used to determine the contact region from the thin bone dataset.

Region of interest (ROI) data which represent a region of interest which is identified as ROI in FIG. 1 and corresponds to at least a part of the vessel V in the vascular structure shown in FIG. 1, are also stored in the memory 3. A number of options for obtaining the ROI data exist.

In accordance with a first option, at least a part of the vessel V is displayed on the output device 6, and the region of interest is manually designated using the input device 5. In accordance with a second option, the name of the vessel V is directly inputted or selected from a list displayed on the output device 6 using the input device 5. The region of interest can then be obtained from a database which stores predefined regions of interest for different vessels. This database can also be stored in the memory 3.

Preferably, all the data mentioned, including the ROI data, the contact region data and where applicable the bone data, are provided in relation to the same reference system, such as for example a reference system defined with respect to the head 10 or preferably a reference system used by the navigation system 7.

In the present example, the region of interest is a three-dimensional volume. However, the region of interest can also be a single point or a plurality of points.

The processing unit 2 acquires the ROI data and the contact region data from the memory 3 and then determines at least one target point in the region of interest. In the present example, the CPU 2 calculates a plurality of uniformly distributed target points in the region of interest. The number of target points can depend on the size of the region of interest, such that neighbouring target points exhibit a particular distance from each other.

The processing unit 2 then determines at least two entry points on the contact region. In the present example, the processing unit 2 creates a mesh of uniformly distributed entry points over the contact region.

The processing unit 2 then calculates a set of lines which comprises the lines between the two points of each respective possible pair consisting of one entry point and one target point. Thus, given n target points and m entry points, this set of lines would contain n×m lines (also referred to as trajectories).

The processing unit 2 then eliminates lines which pass through a bony structure other than the bone immediately beneath the contact region. In a transcranial examination, there will inevitably be a bony structure in the path of the ultrasonic beam between the entry point and the target point, because the ultrasonic beam has to pass through the outer shell of the cranium. However, bony parts of the cranium other than the outer shell may also be in the path of the ultrasonic beam. It is then preferable to eliminate lines which pass through these other bony structures, because the transition from soft tissue to bone and back impairs the results of the examination.

One aim of a transcranial Doppler examination is to determine the speed of the blood flow within a vessel. In order to obtain a reliable Doppler shift in the ultrasound frequency, the angle between the direction of the blood flow at the examined target point and the ultrasonic beam, which is propagated along the line between the entry point and the target point, should lie within a predetermined angular range, such as for example 20 to 60 degrees. The processing unit 2 thus eliminates from the set of lines those for which the intersection angle with the direction of the blood flow at the line's target point is outside the predetermined angular range.

A bifurcation of the vessel, such as the bifurcation B of the vessel V shown in FIG. 1, causes turbulence in the blood flow, which means that a Doppler reading taken at a point close to the bifurcation may not represent the actual blood flow speed in the vessel. The processing unit 2 thus eliminates from the set of lines those for which the target point is closer to the bifurcation B of the vessel V than a minimum bifurcation distance. The minimum bifurcation distance can be selected appropriately, for example as a function of the vessel's diameter. The minimum bifurcation distance can in particular be set to be half, equal to or twice the vessel's diameter.

The processing unit 2 also eliminates from the set of lines all those for which the target point is closer to a vessel other than the vessel represented by the region of interest (in the present example, the second vessel V2) than a predetermined minimum vessel distance, such as for example 0.5 cm, 1 cm or 2 cm. Additionally or alternatively, the processing unit 2 eliminates from the set of lines those which pass a vessel other than the vessel represented by the region of interest (i.e. the second vessel V2 in the present example) at a distance below the predetermined minimum vessel distance or another predetermined distance.

The processing unit 2 then calculates a score for each of the remaining lines in the set of lines. The score is primarily dependent on the intersection angle between the corresponding line and the direction of the blood flow at the line's target point, wherein a small intersection angle results in a high score. The intersection angles are preferably discretised or rounded, for example to integer values, before the score is calculated, i.e. an angle in the range of $\alpha-0.5$ to $\alpha+0.5$ degrees is preferably rounded to an integer value $\alpha$.

The score of a line also depends on the length of a portion of the line which passes through a bony structure. The longer the portion of the line passing through a bony structure, the lower the score of the corresponding line. The intersection angle and the portion of a line passing through a bony structure are preferably weighted in such a way that the line's score is primarily dependent on the intersection angle. If a plurality of lines exhibit the same intersection angle, then the portion of the line which passes through a bony structure is used to determine different scores for these lines. Thus, the influence of the length of the portion of a line which passes through a bony structure cannot override the influence of the intersection angle.

If, for example, all the lines exhibiting the same (discretised or rounded) intersection angle, which is the smallest intersection angle of all the lines in the set of lines, are assigned an intermediate score of 1 and all the other lines are assigned an intermediate score of 0, these intermediate scores can be multiplied by a value which has a negative correlation with the length of the portion of the respective line which passes through a bony structure. Among the lines exhibiting the same (smallest) intersection angle, this means that the line with the shortest length of its portion passing through a bony structure will have the highest score.

The processing unit 2 then selects the entry point of the line with the highest score as the contact position of the ultrasound transceiver 8. This contact position is preferably provided to the navigation system 7 in order to navigate the ultrasound transceiver 8 such that it touches the patient's head 10 at the contact position.

The present invention can also be used to prepare for a therapeutic treatment using ultrasound, wherein the actual therapeutic treatment is not part of the present invention. In such a treatment, the ultrasound transceiver generates an acoustic beam of sufficient power for the purposes of the treatment, for example in order to disintegrate blood clots. In order to increase the effectiveness of the treatment, it is advantageous to simultaneously use a plurality of ultrasonic beams which intersect at the point to be treated. The invention can then be used to calculate the contact positions of a plurality of medical ultrasound transceivers.

For this purpose, a respective contact region is defined for each ultrasound transceiver, and a contact position of the ultrasound transceiver within the respective contact region is calculated, subject to the additional condition that the lines comprising the entry points which have been selected as the contact positions of the ultrasound transceivers must have the same target point or at least target points which exhibit a distance below a predetermined target point distance. Alternatively, this additional condition can be omitted if the region of interest is defined such that the plurality of beams passing through the region of interest achieve the desired therapeutic effect.

LIST OF REFERENCE SIGNS

1 computer
2 central processing unit (CPU)
3 memory
4 interface
5 input device
6 output device
7 medical navigation system
8 ultrasound transceiver
9 marker device
10 head
V vessel
V2 second vessel
B bifurcation

The invention claimed is:
1. A system for assisting optimized positioning of an associated medical ultrasound transceiver on a head of an associated patient for ultrasound imaging a region of interest within the head of the associated patient by the associated medical ultrasound transceiver, the system comprising:
  a memory device;
  logic stored in the memory device; and
  a processor operable to execute the logic stored in the memory device to perform steps for determining an optimum contact position of the associated medical ultrasound transceiver on the head of the associated patient for the ultrasound imaging, the steps comprising:
    acquiring region of interest data, the region of interest data being representative of the region of interest in the head of the associated patient and corresponding to at least a part of a vessel in a vascular structure in the head of the associated patient;
    acquiring a bone dataset, the bone dataset being representative of a three-dimensional bone structure of the head of the associated patient;
    acquiring contact region data, the contact region data being representative of a contact region for the positioning of the associated medical ultrasound transceiver on the head of the associated patient, wherein the contact region corresponds to a location on the head of the associated patient of one or more acoustic windows defined by the three-dimensional bone structure of the head of the associated patient;
    determining at least one target point in the region of interest;
    determining at least two entry points on the contact region;
    determining a set of all possible lines from each of the at least two entry points to each of the at least one target point;
    determining a set of remaining lines by eliminating from the set of all possible lines those lines that pass through a bony structure other than bone structure defining the one or more acoustic windows;
    calculating a score value for each line of the set of remaining lines, wherein the score value represents a suitability of the corresponding line for the ultrasound imaging of the at least one target point;

selecting the entry point of a line with the highest score value as the optimum contact position of the associated ultrasound transceiver for the ultrasound imaging; and providing a signal representative of the optimum contact position to an associated guidance or navigation system providing guidance or navigation information to be followed by an associated user positioning the associated medical ultrasound transceiver on the head of the associated patient for the ultrasound imaging at the optimum contact position.

2. A method for assisting optimized positioning of an associated medical ultrasound transceiver on a head of an associated patient for ultrasound imaging a region of interest within the head of the associated patient by the associated medical ultrasound transceiver, the method comprising executing, on a processor of a computer, steps of:

acquiring by a computer comprising a processing unit operatively coupled with a memory storing a program that is executable by the processor to perform the method region of interest data, the region of interest data being representative of the region of interest in the head of the associated patient and corresponding to at least a part of a vessel in a vascular structure in the head of the associated patient;

acquiring by the computer a bone dataset, the bone dataset being representative of the three-dimensional bone structure of the head of the associated patient;

acquiring by the computer contact region data, the contact region data being representative of a contact region for the positioning of the associated medical ultrasound transceiver on the head of the associated patient, wherein the contact region corresponds to a location on the head of the associated patient of one or more acoustic windows defined by the three-dimensional bone structure of the head of the associated patient;

determining by the computer at least one target point in the region of interest;

determining by the computer at least two entry points on the contact region;

determining by the computer a set of all possible lines extending from each of the at least two entry points to the at least one target point;

determining by the computer a set of remaining lines by eliminating from the set of all possible lines those lines that pass through a bony structure other than bone structure defining the one or more acoustic windows;

calculating by the computer a score value for each line of the set of remaining lines, wherein the score value represents a suitability of the corresponding line for the ultrasound imaging of the at least one target point;

selecting by the computer the entry point of a line with the highest score value as an optimum contact position of the ultrasound transceiver for the ultrasound imaging; and providing by an interface of the computer a signal representative of the optimum contact position to an associated guidance or navigation system providing guidance or navigation information to be followed by an associated user positioning the associated medical ultrasound transceiver on the head of the associated patient for the ultrasound imaging at the optimum contact position.

3. The method according to claim 2, wherein the determining the set of remaining lines by the eliminating comprises:

eliminating from the set of all possible lines:

lines having an intersection angle relative to a direction of the blood flow in the at least the part of the vessel in the vascular structure in the head of the associated patient at the lines' target point being outside a predetermined angular range.

4. The method according to claim 2, wherein the calculating the score value of a line comprises calculating the score value of a line based on a difference between:

an intersection angle of the line with a direction of blood flow in the at least the part of the vessel in the vascular structure in the head of the associated patient at the line's target point and a predetermined angle.

5. The method according to claim 2, wherein the calculating the score value of a line comprises calculating the score value of a line based on a length of a portion of the line that passes through a bony structure.

6. The method according to claim 2, wherein the determining the set of remaining lines by the eliminating comprises:

eliminating from the set of all possible lines:

lines having a target point closer to a bifurcation of the at least the part of the vessel in the vascular structure in the head of the associated patient than a predetermined minimum bifurcation distance.

7. The method according to claim 2, wherein the calculating the score value of a line comprises calculating the score value of a line based on a distance between the line's target point and a bifurcation of the at least the part of the vessel in the vascular structure in the head of the associated patient.

8. The method according to claim 2, wherein the determining the set of remaining lines by the eliminating comprises:

eliminating from the set of all possible lines:

lines having a target point closer to a vessel other than the vessel in the vascular structure in the head of the associated patient represented by the region of interest than a predetermined minimum vessel distance.

9. The method according to claim 2, wherein the calculating the score value of a line comprises calculating the score value of a line based on a distance between the line's target point and a vessel in the vascular structure in the head of the associated patient other than the at least the part of the vessel represented by the region of interest data.

10. The method according to claim 2, wherein acquiring the contact region data comprises:

generating an eroded bone dataset by performing a morphological erosion of the bone dataset by a predetermined thickness;

performing a morphological dilation of the eroded bone dataset by the predetermined thickness;

subtracting the dilated bone dataset from the original bone dataset to obtain a difference dataset; and using a difference dataset as the contact region data.

11. The method according to claim 2, further comprising:

acquiring a plurality of contact regions; and calculating a contact position of the associated medical ultrasound transceiver for each of the plurality of contact regions.

12. The method according to claim 2, wherein:

the step of acquiring the region of interest data comprises acquiring a plurality of region of interest data for a corresponding plurality of regions of interest;

a set of lines is calculated for each of the plurality of regions of interest by repeating the step of determining by the computer the set of all possible lines extending from each of the at least two entry points to the at least one target point a determined number of times;

one line is selected from each set of lines, such that the selected lines have a common entry point and combined score values of the selected lines is maximized; and the step of selecting the entry point of the line with the highest score value as the optimum contact position comprises selecting the common entry point as the contact position of the associated medical ultrasound transceiver.

13. The method according to claim 12, further comprising determining a plurality of alternative contact positions if no single entry point has lines leading to each of the plurality of regions of interest.

14. The method according to claim 2, wherein:

the step of acquiring the region of interest data comprises acquiring a plurality of region of interest data for a corresponding plurality of regions of interest;

the step of determining at least one target point in the region of interest comprises determining at least one target point in each of the plurality of regions of interest;

the step of determining the set of all possible lines extending from each of the at least two entry points to the at least one target point comprises determining the set of all possible lines which comprises the lines between the two points of each respective possible pair consisting of one entry point and one target point from the target points in all the regions of interest;

a set of entry points comprising only the entry points which have remaining lines leading to each of the regions of interest is calculated;

for each entry point in the set of entry points, a subset of lines is calculated, wherein the subset of lines comprises only one line from the corresponding entry point to each of the regions of interest, such that the combined score values for the lines in the subset of lines is maximized; and the step of selecting the entry point of the line with the highest score value as the optimum contact position comprises selecting the entry point for which the subset of lines has the largest combined score value as the contact position of the ultrasound transceiver.

15. The method according to claim 14, further comprising determining a plurality of alternative contact positions if no single entry point has lines leading to each of the plurality of regions of interest.

16. A non-transitory computer-readable storage medium storing a computer program which, when executed by a processing unit of a computer, causes the processing unit of the computer to perform a method for assisting optimized positioning of an associated medical ultrasound transceiver on a head of an associated patient for ultrasound imaging a region of interest within the head of the associated patient by the associated medical ultrasound transceiver, the method comprising:

acquiring region of interest data, the region of interest data being representative of the region of interest in the head of the associated patient and corresponding to at least a part of a vessel in a vascular structure in the head of the associated patient;

acquiring a bone dataset, the bone dataset being representative of the three-dimensional bone structure of the head of the associated patient;

acquiring contact region data, the contact region data being representative of a contact region for the positioning of the associated medical ultrasound transceiver on the head of the associated patient, wherein the contact region corresponds to a location on the head of the associated patient of one or more acoustic windows defined by the three-dimensional bone structure of the head of the associated patient;

determining at least one target point in the region of interest;

determining at least two entry points on the contact region;

determining a set of all possible lines extending from the at least two entry points to the at least one target point;

determining a set of remaining lines by eliminating from the set of all possible lines those lines that pass through a bony structure other than bone structure defining the one or more acoustic windows;

calculating a score value for each line of the set of remaining lines, wherein the score value represents a suitability of the corresponding line for the ultrasound imaging of the at least one target point; and selecting the entry point of the line with the highest score value as an optimum contact position of the ultrasound transceiver for the ultrasound imaging; and providing a signal representative of the optimum contact position to an associated guidance or navigation system providing guidance or navigation information to be followed by an associated user positioning the associated medical ultrasound transceiver on the head of the associated patient for the ultrasound imaging at the optimum contact position.

* * * * *